United States Patent
Kim et al.

(10) Patent No.: US 7,620,450 B2
(45) Date of Patent: Nov. 17, 2009

(54) METHOD AND SYSTEM FOR REMOVING NOISE BY USING CHANGE IN ACTIVITY PATTERN

(75) Inventors: Youn Ho Kim, Hwaseong-si (KR); Kun Soo Shin, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 650 days.

(21) Appl. No.: 11/401,943

(22) Filed: Apr. 12, 2006

(65) Prior Publication Data

US 2007/0173734 A1    Jul. 26, 2007

(30) Foreign Application Priority Data

Oct. 7, 2005    (KR)    ........................ 10-2005-0094310

(51) Int. Cl.
*A61B 5/04*    (2006.01)
*A61B 5/103*    (2006.01)
(52) U.S. Cl. ..................................... 600/546; 600/595
(58) Field of Classification Search .................. 600/511
See application file for complete search history.

(56) References Cited

U.S. PATENT DOCUMENTS 5,209,237 A * 5/1993 Rosenthal .................... 600/511
2005/0267376 A1* 12/2005 Marossero et al. ........... 600/511

* cited by examiner

*Primary Examiner*—Carl H. Layno
*Assistant Examiner*—Jon-Eric C. Morales
(74) *Attorney, Agent, or Firm*—Staas & Halsey LLP

(57) ABSTRACT

A noise removal method and system using a change in activity pattern, in which it is recognized that noise components exist in different frequency bands and different filters for removing noise are stored according to each activity pattern, thereby optimally removing the noise components. A method of removing noise by using a change in an activity pattern includes: recognizing an activity pattern of the subject using an activity sensor; sensing a first bio signal corresponding to the activity pattern from the subject using an electric potential sensor; recognizing a noise generation pattern according to the activity pattern by analyzing a noise component for each section of the first bio signal; selecting filter information for each section according to the noise generation pattern; storing the filter information selected for each section in association with the activity pattern; and removing noise from a second bio signal sensed from the subject by applying the stored filter information.

11 Claims, 4 Drawing Sheets

FIG. 3A  Y-AXIS OF TRI-AXIAL ACCELEROMETER
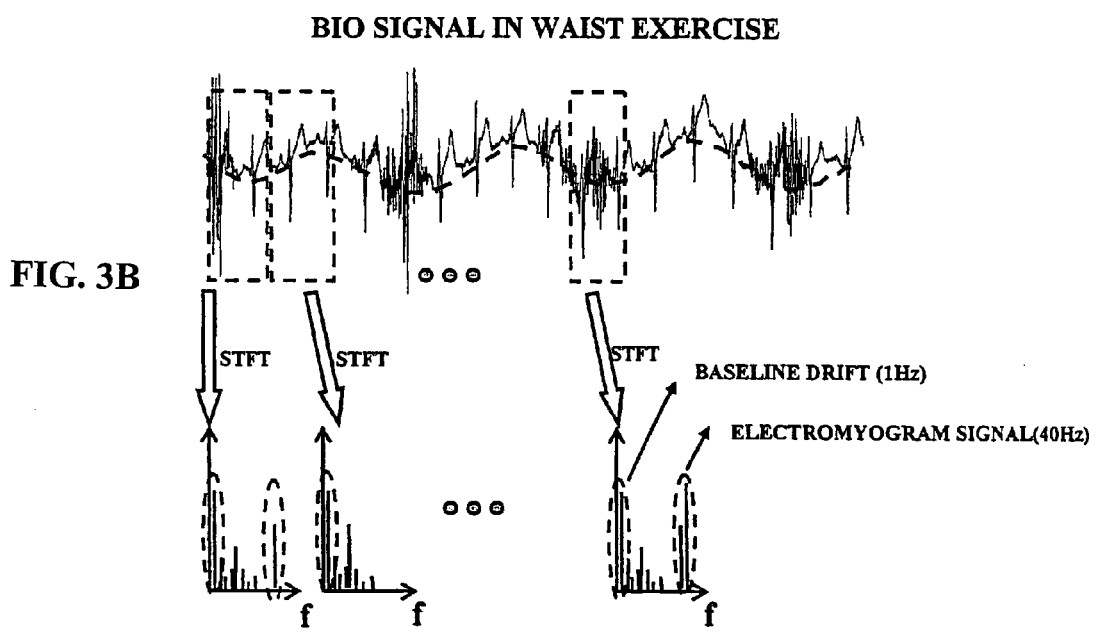
FIG. 3B  BIO SIGNAL IN WAIST EXERCISE
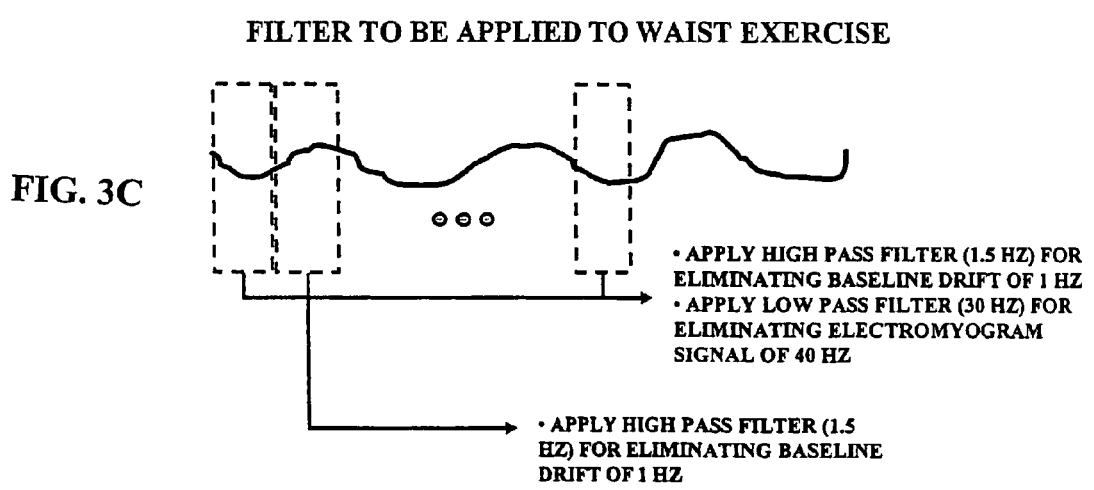
FIG. 3C  FILTER TO BE APPLIED TO WAIST EXERCISE
- APPLY HIGH PASS FILTER (1.5 HZ) FOR ELIMINATING BASELINE DRIFT OF 1 HZ
- APPLY LOW PASS FILTER (30 HZ) FOR ELIMINATING ELECTROMYOGRAM SIGNAL OF 40 HZ
- APPLY HIGH PASS FILTER (1.5 HZ) FOR ELIMINATING BASELINE DRIFT OF 1 HZ

METHOD AND SYSTEM FOR REMOVING NOISE BY USING CHANGE IN ACTIVITY PATTERN

CROSS-REFERENCE TO RELATED APPLICATION

This application claims the benefit of Korean Patent Application No. 2005-94310, filed on Oct. 7, 2005, in the Korean Intellectual Property Office, the disclosure of which is incorporated herein by reference.

BACKGROUND OF THE INVENTION

1. Field of the Invention

The present invention relates to a method and system for removing noise by using a change in activity pattern, in which it is recognized that an occupation pattern of a noise component included in a bio signal is different according to the activity pattern of the subject and different filters for removing noise according to each activity pattern are stored, thereby optimally removing the noise components.

2. Description of Related Art

A general sensing device for measuring a bio signal is attached to a subject such as a human and directly senses a bio signal such as an electrocardiogram signal of the subject. The sensed bio signal is used as data for determining whether there is an abnormality in the subject, via a predetermined analysis procedure. For example, when sensing an electrocardiogram signal, the electrocardiogram signal may be assessed only for whether cardiac impulse of the subject is normal and the stress load on the subject.

However, when a patch type sensor attached directly on the subject, the strength of a sensed electrocardiogram signal is less than a standard electrocardiogram and the frequency of generating an electromyogram signal acting as noise according to a position to which the sensor is attached is increased.

In addition, frequency components of noise generated according to the movement of the subject in an electrocardiogram signal are different from each other. In this case, an optimal filter for removing the frequency components generated according to the relevant movement has to be selected and applied.

For example, in an activity pattern of the subject, such as walking, jogging, and running, a noise component such as an electromyogram signal higher than 30 Hz is generated. Therefore, a filter passing a signal of less than 30 Hz has to be applied in order to remove this noise component.

On the other hand, with respect to the activity pattern of the subject performing back or stomach exercises, a noise component of the electromyogram signal continuously occurs below 0.5 Hz. In order to remove this noise component, a filter passing signals higher than 0.5 Hz has to be applied If a filter to be applied is previously determined by considering the activity pattern of the subject, the filter may be automatically determined by recognizing the relevant activity pattern of the subject by actually sensing a bio signal, the burden of continuously changing filters may be solved.

Also, when a patch type electric potential measurement sensor, an electrocardiogram signal is weak and relatively susceptible to an electromyogram signal and baseline drift. This may be a problem generated in using any minimized electrodes. Particularly, since noises such as the electromyogram signal and baseline drift have a tendency in which patterns of noise components are different according to activity pattern, if the respective effects on the electrocardiogram according to the activity pattern is recognized, noise may be effectively removed.

Accordingly, a method of removing noise in which a previously determined filter for removing noise is selected according to the activity pattern of the subject, thereby eliminating baseline drift and electromyogram noise in sensing an electrocardiogram is required.

BRIEF SUMMARY

An aspect of the present invention provides a noise removal method and system using a change in activity pattern, in which a filter for removing noise components included in a bio signal is selected according to activity pattern of the subject, thereby removing baseline drift and an electromyogram signal when sensing an electrocardiogram signal.

An aspect of the present invention also provides a noise removal method and system using a change in activity pattern, in which a filter required in removing noise is determined by analyzing a part of bio signals sensed from the subject and the determined filter is applied to a sensed bio signal, thereby quickly removing the noise.

An aspect of the present invention also provides a noise removal method and system using a change in activity pattern, in which a bio signal is converted from a time domain into a frequency domain to identify a frequency band which includes a noise component and to easily determine a filter filtering the noise component in the frequency band.

According to an aspect of the present invention, there is provided a method of removing noise by using a change in an activity pattern, including: recognizing an activity pattern of the subject by using an activity sensor; sensing a first bio signal corresponding to the activity pattern from the subject by using an electric potential sensor; recognizing a noise generation pattern according to the activity pattern by analyzing a noise component for each section of the first bio signal; selecting filter information for each section according to the noise generation pattern; storing the filter information selected for each section in association with the activity pattern; and removing noise from a second bio signal sensed from the subject by applying the stored filter information.

According to another aspect of the present invention, there is provided a system for removing noise by using a change in an activity pattern, including: a motion sensing unit recognizing an activity pattern of the subject by using an activity sensor; a bio sensing unit sensing a first bio signal corresponding to the activity pattern from the subject by using an electric potential sensor; a filter information generation unit recognizing a noise generation pattern according to the activity pattern by analyzing a noise component for each section of the first bio signal and selecting filter information for each section according to the noise generation pattern; and a filtering unit storing the filter information selected for each section in association with the activity pattern and removing noise from a second bio signal sensed from the subject by applying the stored filter information.

According to another aspect of the present invention, there is provided a computer-readable storage medium encoded with processing instructions for causing a processor to execute the aforementioned method.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which:

FIGS. 3A-3C are diagrams illustrating a process of selecting filter information, according to an embodiment of the present invention.

DETAILED DESCRIPTION OF EMBODIMENTS

Figure 1:
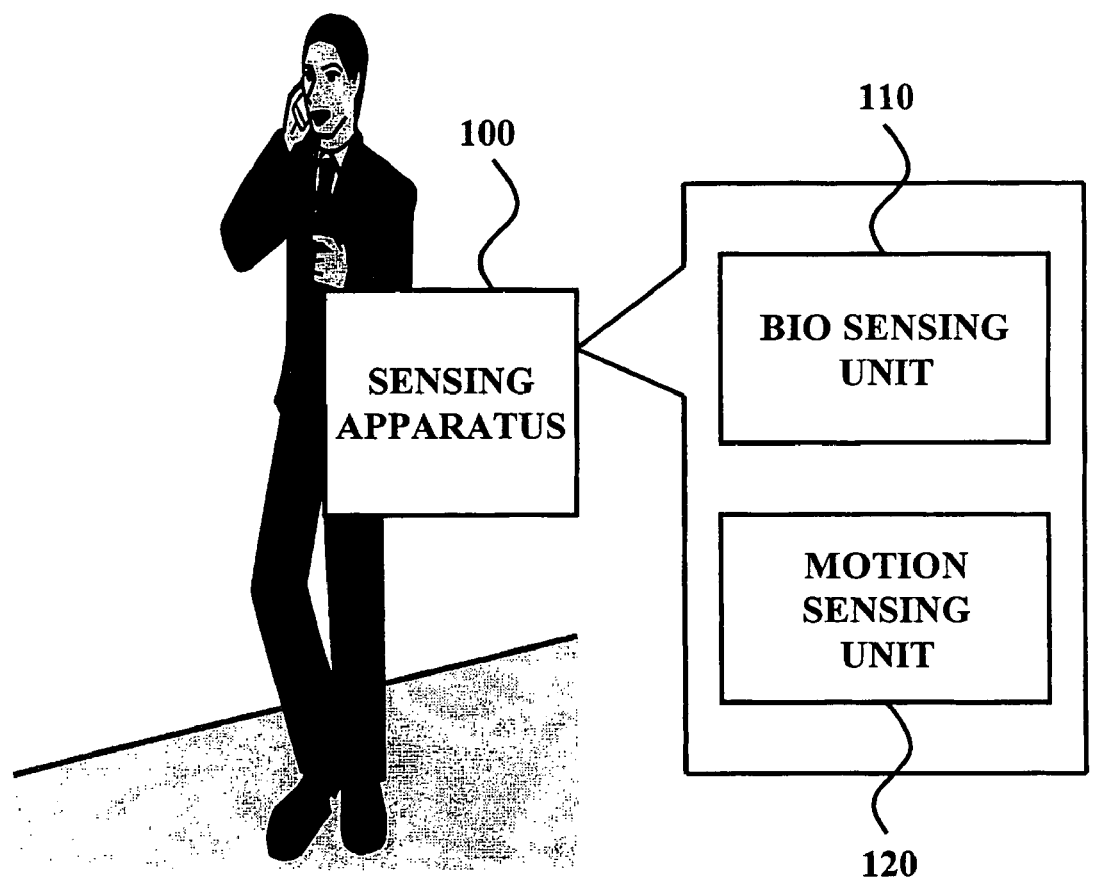
FIG. 1 is a block diagram illustrating an example of a sensing apparatus for sensing a bio signal, according to an embodiment of the present invention.

Reference will now be made in detail to embodiments of the present invention, examples of which are illustrated in the accompanying drawings, wherein like reference numerals refer to the like elements throughout. The embodiments are described below in order to explain the present invention by referring to the figures.

In the following description, it is assumed that a pattern of a bio signal sensed from a subject has a regular shape, a filter required in removing noise by analyzing a first bio signal is determined and the filter is applied to remove a second bio signal, thereby effectively removing noise.

The first bio signal and the second bio signal are divided for convenience of explanation in the description that follows. However, the first bio signal and the second bio signal may be the same bio signal. According to various embodiments, the first bio signal may be a bio signal sampled for determining a filter and the second bio signal may be a bio signal measured after the sampling of the first bio signal.

Particularly, in the description that follows, the activity pattern of the subject is recognized by considering acceleration of motion of the subject, measured by a sensing device having acceleration sensor function, and by sensing a typical electrocardiogram signal for the recognized activity pattern. However, a frequency component of noise included in the sensed electrocardiogram signal may vary according to the activity pattern of the subject. Accordingly, a noise removal system of embodiments of the present invention applies a filter which can remove baseline drift or an electromyogram signal that is determined to be noise in the electrocardiogram measurement, according to each activity pattern of the subject and removes the noise components.

FIG. 1 is a block diagram illustrating an example of a sensing apparatus 100 for sensing a bio signal, according to an embodiment of the present invention. Later, a patch type sensing apparatus attached to the subject to sense a bio signal and recognize an activity pattern of the subject will be described in detail.

The sensing apparatus 100 of the present embodiment may include a bio sensing unit 110 and a motion sensing unit 120. As described above, the sensing apparatus 100 may be embodied as a patch type which is detachable, attached to a part of the body of the subject.

The bio sensing unit 110 senses a bio signal, which is an electric potential signal such as an electromyogram signal, from the subject. Particularly, the bio sensing unit 110 may recognize the body portion at which the bio signal of the subject is sensed and may selectively sense a bio signal corresponding to the recognized result. For example, in order to measure the stress index of the subject, the sensing unit 110 may sense an electrocardiogram signal at the chest of the subject while the subject takes a rest which may improve reliability of sensing.

In the present embodiment, it is described that a position of the bio sensing unit 110 sensing an electrocardiogram signal, according to the goals of the present embodiment, is the chest of the subject. However, this description is for convenience and does not define the scope of the present embodiment. Also, the electric potential signal may be defined as a bio signal corresponding to the recognized result from bio signals which can be sensed from the subject that is an object to be measured.

The motion sensing unit 120 recognizes an activity pattern of the subject and senses a motion of the subject over time. The motion sensing unit 120 may include a plurality of sensing devices. For example, the motion sensing unit 120 may be formed by integrating a plurality of sensing devices as one patch type that is detachable. Also, the plurality of the sensing devices may be connected via a circuit network while separated from each other. For example, each of the sensing devices may be in a different position and may be connected to each other via the same circuit network. The sensing device may have a function as an acceleration sensor and senses accelerated motion of the subject in the directions of x, y, and z axes via the acceleration sensor. There may be resting, walking, or running as activity patterns of the subject, sensed by the motion sensing unit 120.

Namely, the sensing apparatus 100 of the present embodiment recognizes the activity patterns of the subject and senses an electrocardiogram signal generated according to each of the activity patterns by using the described sensing unit 110 and the motion sensing unit 120.

The sensing apparatus 100 according to the present embodiment may include a noise removal system 200 (shown in FIG. 2) or be separate from the noise removal system 200, which may be designed in view of system environments.

However, the bio sensing unit senses all bio signals which can be sensed at the position to which the sensing apparatus 100 is attached, for example, at the chest of the subject. As a result, a baseline drift or an electromyogram signal functioning as noise may exist in the bio signals sensed by the bio sensing unit 110, in addition to an electrocardiogram signal that is the object to be measured. Accordingly, in order to separate only an electrocardiogram signal from the bio signals, a process of removing the noise components is required. For this, in the present embodiment, filter information for designating a filter to be applied for each section of a predetermined size, which divides the bio signal is generated, thereby removing the noise in a relevant section by using the filter information.

Hereinafter, referring to FIG. 2, the method of the noise removal system 200 which removes the noise components from the bio signals sensed by the sensing apparatus 100 will be described in detail.

Figure 2:
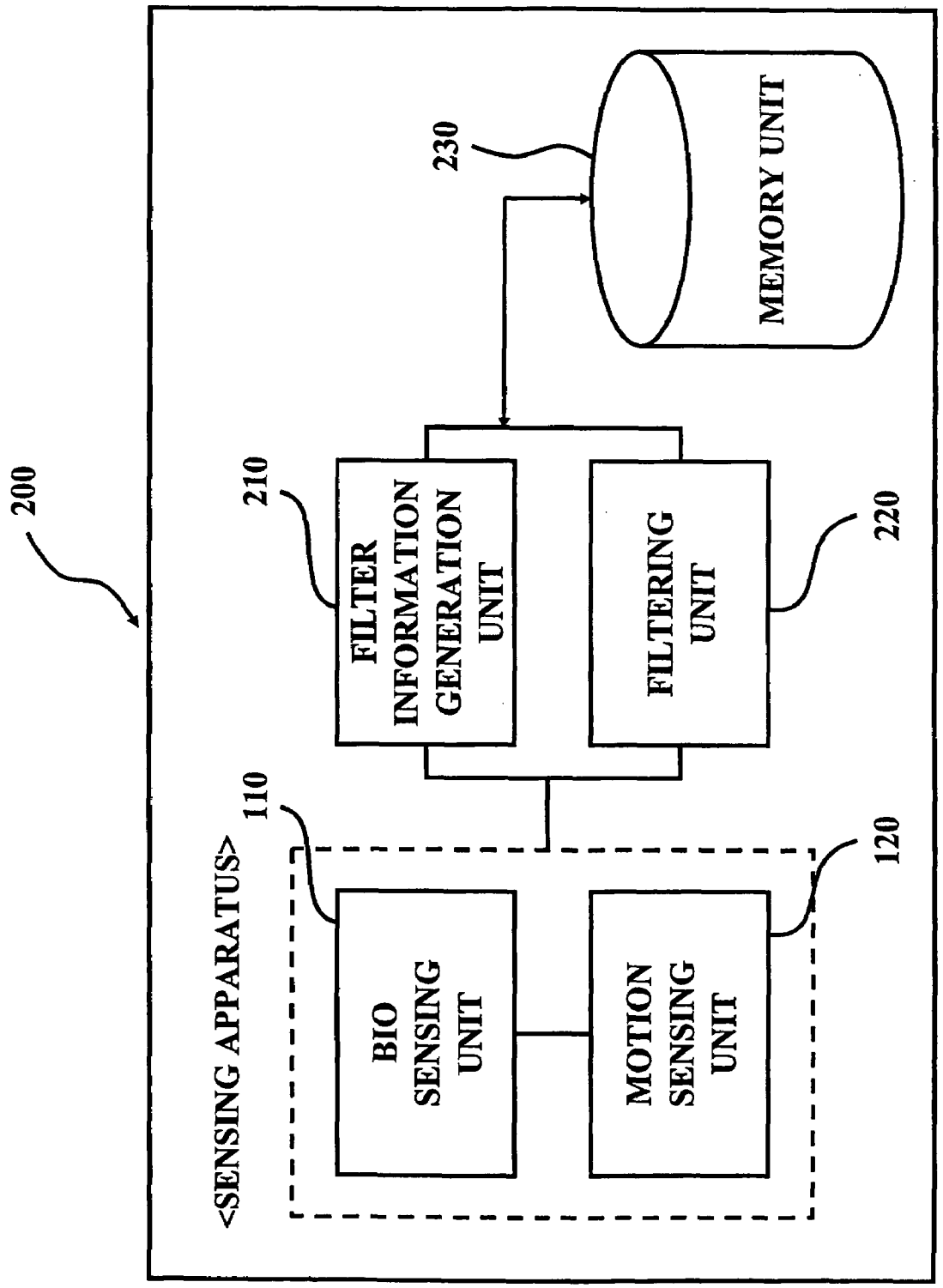
FIG. 2 is a configuration diagram illustrating a noise removal system according to an embodiment of the present invention.

FIG. 2 is a configuration diagram illustrating the noise removal system 200 according to an embodiment of the present invention.

As described above, the noise removal system 200 is a detachable patch type and may be formed by being integrated with the sensing apparatus 100. The present embodiment will be described by defining the described noise removal system 200. However, the definition is for convenience of description, and the noise removal system 200 may be embodied as being separated from the sensing apparatus 100 according to system environments.

The noise removal system 200 may include the motion sensing unit 120 and bio sensing unit 110 of the sensing apparatus 100, a filter information generation unit 210, a filtering unit 220, and a memory unit 230.

The motion sensing unit 120 is included in the patch type sensing apparatus 100 and recognizes the activity pattern of the subject by considering a motion of the subject and an acceleration of the motion. Namely, the motion sensing unit 120 recognizes the activity pattern of the subject by using a motion sensor. The activity pattern of the subject may be determined by the acceleration of the sensor and the recognition by the motion sensing unit 120 of the subject's acceleration motion in the direction of the X, Y, and Z axes. For example, the motion sensing unit 120 is formed of sensing devices with respect to one subject sensing a bio signal in a plurality of positions at the same time, may compute each acceleration motion result of the subject by the acceleration motion of each sensing device, and may recognize the activity pattern of the subject by using an optimal result from the computation result. There may be resting, walking, jogging, running, and exercising as the activity patterns recognized by the motion sensing unit 120.

The bio sensing unit 110 senses a first bio signal corresponding to the recognized activity pattern of the subject. Namely, the bio sensing unit 110 senses a first bio signal corresponding to the activity pattern of the subject by using a predetermined electric potential sensor. In this case, the first bio signal designates a bio signal collected by sampling of a predetermined size from sensed bio signals and may signify a bio signal of a sufficient length of time capable of analyzing noise components included in the bio signal. The length of time associated with the first bio signal is not particularly defined and may vary.

The filter information generation unit 210 recognizes a noise generation pattern according to the activity pattern by analyzing a noise component for each section of the first bio signal and selects filter information for each section according to the noise generation pattern. Namely, the filter information generation unit 210 identifies a noise component for each section of the sensed first bio signal and determines a filter for removing the identified noise component. Also, the filter information generation unit 210 may generate filter information by associating the determined filter with the section of identifying the noise component.

In generating the filter information, the filter information generation unit 210 divides the first bio signal sensed from the subject into sections based on a predetermined standard, for example, a certain length of time, and performs a predetermined noise sensing process for determining whether a noise component exists in each section. In this case, the first bio signal may be sensed during a motion of the subject for a certain period of time and may be displayed in a time domain. It may be not easy to determine a filter for identifying a frequency band of a noise component, or filtering a bio signal in a specified frequency band in the bio signal in the time domain. The filter information generation unit 210 of the present embodiment designates a filter for an identified frequency band which includes the noise component and eliminates the noise component in the identified frequency band which is accomplished by converting the sensed first bio signal from a time domain into a frequency domain.

In the present embodiment, a bio signal is divided into sections according to a predetermined standard and each of the sections is converted into a frequency domain. However, from the sensed bio signals of the subject, a certain section of the bio signal, which is determined to include a noise component through making a signal conspicuous, may be selected and converted.

As a method of converting the bio signal from the time domain into the frequency domain, a kind of Fourier transform known as short time Fourier transform (STFT), or wavelet conversion may be used. Also, in order to pass only a frequency band of an electrocardiogram signal that is an object to be measured, in other words, excluding the frequency band identified to be the noise, the filter information generation unit 210 may generate filter information to eliminate baseline drift functioning as noise by applying a high pass filter (HPF) and eliminate an electromyogram signal as another noise by applying a low pass filter (LPF).

In addition, the filter information generation unit 210 records and maintains the filter information generated by analyzing the first bio signal, which corresponds to the activity pattern of the subject, in the memory unit 230. The maintenance of the filter information is for searching filter information corresponding to a relevant activity pattern from the filter information previously stored in the memory unit 230 and subsequently eliminating the noise of the bio signal at one time by using the searched filter information.

In this case, the memory unit 230 is a kind of a storage means in which information on a filter to be applied in sensing an electrocardiogram signal, with respect to an activity pattern according to various activities of the subject, is recorded. Also, in sensing an electrocardiogram signal in the present embodiment, in the memory unit 230, filter information of determining a filter capable of optimally eliminating baseline drift or an electromyogram signal, which is a noise component, from bio signals sensed from the subject is recorded corresponding to each of the activity patterns.

FIGS. 3A-3C are diagrams illustrating a process of selecting filter information, according to an embodiment of the present invention.

In FIGS. 3A-3C, when the subject is actually performing an exercise involving the waist (hereinafter "waist exercise"), the motion sensing unit 120 of FIG. 2 recognizes an activity pattern of the subject as waist exercise and determines a filter capable of eliminating a noise component from bio signals sensed in the recognized waist exercise, thereby selecting filter information.

In FIG. 3A, a pattern of a bio signal sensed by the patch type sensing apparatus 100 attached to the subject performing waist exercise is shown. Viewing a part of the acceleration motion result, for example, a Y axis pattern of tri-axial accelerometer is determined to be the activity pattern of the subjecting performing the waist exercise from the acceleration motion result sensed by a plurality of sensing devices. As shown in FIG. 3A, the activity pattern associated with the waist exercise of the subject may be shown as an approximate sine wave.

In FIG. 3B, a bio signal corresponding to the determined activity pattern is sensed by the bio sensing unit 110 and a noise component is identified by using the bio signal. The filter information generation unit 210 of FIG. 2 receives a bio signal corresponding to the activity pattern which is determined to be associated with waist exercise and receives a bio signal moving as a sine similar to the activity pattern recognized by the sensing apparatus 100 as shown in FIG. 3B. Also, the filter information generation unit 210 compares the recognized activity pattern with the sensed bio signal by overlaying the standardized activity pattern and the sensed bio signal, and then determines the bio signal contains noise, and finally identifies the bio signal in a relevant time domain.

The filter information generation unit 210 of FIG. 2 performs STFT or wavelet transform, which converts the selected bio signal from the time domain into the frequency domain, thereby identifying the frequency band of the noise component included in the bio signal. Namely, the filter information generation unit 210 indicates the frequency band of baseline drift or an electromyogram signal, which functions as a noise component, thereby easily identifying a frequency band in which the noise component is located.

For example; the filter information generation unit 210 of FIG. 2 may recognize that a baseline drift of 1 Hz and an electromyogram signal, which functions as a noise component, of 40 Hz exist in a bio signal in the descending part of the bio signal as noise, after performing STFT or wavelet transform with respect to the descending part of the bio signal sensed from the subject performing waist exercise referring to ii) of FIG. 3. A section including the identified noise component may be shown in every period as the bio signal performs sine movement. As a result, when a relevant bio signal is continuously sensed by the sensing apparatus 100, the baseline drift of 1 Hz and the electromyogram signal, which functions as a noise component, of 40 Hz are always included in the bio signal at the descending part of the sine curve.

Also, the filter information generation unit 210 of FIG. 2 may also perform STFT or wavelet transform on a bio signal at an ascending part of the sine curve and may identify that the baseline drift of 1 Hz exists as noise in the bio signal.

In FIG. 3C, a filter to be applied for each particular section of the bio signal is determined and a result of the determination is the filter information. Namely, the filter information generation unit 210 determines a filter for optimally removing a noise component included in a bio signal, for each particular section and may select filter information by using this determination.

For example, the filter information generation unit 210 of FIG. 2 applies a HPF passing only signals in a frequency band higher than 1 Hz, to a bio signal corresponding to the descending part of the sine curve, thereby removing baseline drift of 1 Hz from the bio signal. In this example, in the HPF, a lower limit is set as 1.5 Hz. In addition, the filter information generation unit 210 applies a LPF passing only signals in a frequency band lower than 40 Hz, thereby removing electromyogram signals of 40 Hz from the bio signal. In this example, in the LPF, an upper limit is set as 30 Hz.

As another embodiment, the filter information generation unit 210 applies a band pass filter (BPF) passing only 1.5 to 30 Hz to the bio signal corresponding to the descending part of the sine curve, instead of the HPF and LPF, thereby detecting only an electrocardiogram signal.

Also, the filter information generation unit 210 applies the HPF to a bio signal corresponding to the ascending part of the sine curve, thereby removing baseline drift of 1 Hz from the bio signal. In this example, in the HPF, a lower limit is set as 1.5 Hz.

As a result, with respect to the waist exercise that is the activity pattern of the subject, the filter information generation unit 210 generates filter information in which a HPF of 1.5 Hz and a LPF of 30 Hz are designated as filters to be applied and records and maintains the filter information in the memory unit 230.

Also, the filter information generation unit 210 may generate filter information with respect to other activities of the subject in a method similar to the described waist exercise. For example, with respect to walking, jogging, and running, the filter information generation unit 210 may recognize that an electromyogram signal that is noise occurs at 30 Hz and may generate filter information by designating a LPF whose upper limit is set as 25 Hz, as a filter for removing the noise.

Also, with respect to a back-stomach exercise of the subject, the filter information generation unit 210 may recognize that baseline drift that is noise occurs at 0.5 Hz and may generate filter information by designating a HPF whose lower limit is set as 1 Hz, as a filter for removing the noise.

Also, the filter information generation unit 210 records and maintains the generated filter information in the memory unit 230 in response to the activity pattern of the subject, recognizes the activity pattern of the subject when a bio signal is sensed from the subject, and enables filter information corresponding to the recognized activity pattern to be searched from the memory unit 230. As a result, noise of a bio signal may be removed by using previously generated filter information, thereby more easily and quickly removing the noise.

The filtering unit 220 enables a process of removing noise with respect to a second bio signal sensed from the subject at one time by using the generated filter information. Namely, the filtering unit 220 stores the filter information selected for each section of the bio signal in the memory unit 230 in association with the activity pattern and removes noise from a second bio signal sensed from the subject by applying the stored filter information.

For example, with respect to a second bio signal sensed from the subject performing waist exercise, the filtering unit 220 a HPF whose lower limit is set as 1.5 Hz and a LPF whose upper limit is set as 30 Hz by using the generated filter information, thereby removing baseline drift and electromyogram signal, which functions as a noise component, included in a bio signal.

In addition, when a new bio signal is received from a predetermined subject, the filtering unit 220 may search the generated filter information from the memory unit 230 by only recognizing the activity pattern of the relevant subject and enables the process of removing noise from the bio signal to be performed by using the searched filter information.

Namely, the filtering unit 220 may search filter information corresponding to the activity pattern recognized by the motion sensing unit, with respect to the subject whose bio signal is sensed, from the memory unit 230 and may remove noise from the bio signal by applying a filter designated by the searched filter information with respect to a particular section of the bio signal. For example, when the activity pattern of the subject whose bio signal is being sensed is recognized as waist exercise, the filtering unit 220 may search filter information corresponding to the waist exercise from the previously generated filter information and may remove a noise component from the received bio signal by using the searched filter information.

Hereinafter, a noise removal method according to an embodiment of the present invention will be described in detail.

Figure 4:
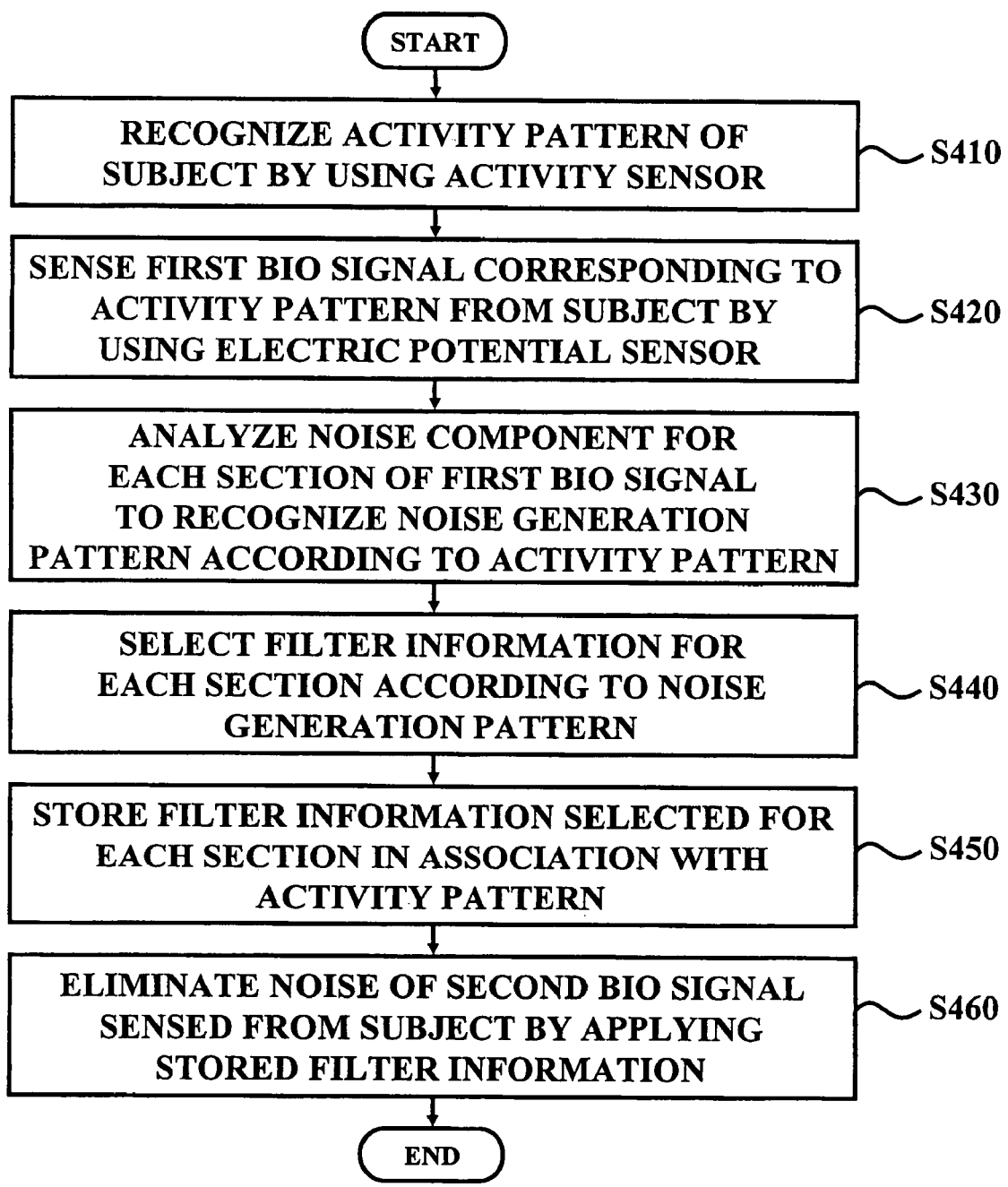
FIG. 4 is a flowchart illustrating a noise removal method according to an embodiment of the present invention.

FIG. 4 is a flowchart illustrating the noise removal method according to an embodiment of the present invention.

The noise removal method of the present embodiment may be performed by the described noise removal system 200 and is, for ease of explanation, explained hereafter with concurrent reference to FIGS. 2 and 4.

The noise removal system 200 recognizes activity pattern of the subject by using an activity sensor (Operation 410). In Operation 410, the activity pattern of the subject is recognized by using an acceleration motion of the subject. For example, the activity pattern of the subject may be sensed as resting, walking, jogging, running, and exercising by analyzing a result of the acceleration motion sensed by an acceleration sensor. As described above, the acceleration sensor may be embodied as a patch attached to the subject, which is detachable, and may measure a result of an acceleration motion of the subject in the directions of the X, Y, and Z axes by a plurality of sensing devices.

Also, the noise removal system 200 senses a first bio signal corresponding to the activity pattern from the subject by using an electric potential sensor (Operation 420). In Operation 420, bio signals from the subject are sensed, the first bio signal is selected by sampling a predetermined amount of bio signal of the sensed bio signals, and the first bio signal is received as an electric potential signal. The time period may be selected to be sufficient for detecting noise components included in the bio signal and may vary.

The noise removal system 200 analyzes a noise component for each section of the first bio signal to recognize a noise generation pattern according to the activity pattern (Operation 430). In Operation 430, the pattern of the noise component is recognized by checking the section of the bio signal, including the noise, by comparing the activity pattern of the subject with the sensed bio signal by overlapping. Also, with respect to the section determined to include the noise, the noise removal system 200 converts a relevant bio signal from a time domain into a frequency domain, thereby easily determining a frequency band occupied by the noise component. Namely, the noise removal system 200 converts the first bio signal sensed according to the lapse of time and displayed as the time domain by STFT or wavelet transform to display as the frequency domain. Accordingly, according to the present embodiment, noise such as baseline drift or electromyogram signal, which functions as a noise component, may be displayed as the frequency domain, in addition to the electrocardiogram signal included in the bio signal (as shown in FIG. 3B).

Also, the noise removal system 200 selects filter information for each section according to the noise generation pattern (Operation 440). In Operation 440, according to as the frequency band occupied by the noise component such as baseline drift or electromyogram signal, which functions as a noise component, is determined in Operation 430, a filter eliminating signals in the frequency band is determined. For example, the noise removal system 200 may determine a HPF passing signals higher than 1.5 Hz as a filter for eliminating baseline drift of 1 Hz and may determine a LPF passing signals lower than 30 Hz as a filter for eliminating an electromyogram signal of 40 Hz (S FIGS. 3A-3C).

Namely, the noise removal system 200 may determine a filter capable of selecting a pure electrocardiogram signal from the sensed bio signal and may select the filter as filter information.

The noise removal system 200 stores the filter information selected for each section in association with the activity pattern (Operation 450). In Operation 450, the filter information associated with determining the applied filter which corresponds to the activity pattern of the subject is stored in the memory unit 230.

Also, the noise removal system 200 removes noises of a second bio signal sensed from the subject by applying the stored filter information (Operation 460). In Operation 460, the noises with respect to the second bio signal are removed at one time based on the filter information designating the filter applied to each section of the bio signal.

In addition, when a new bio signal is sensed from a predetermined subject by using the filter information recorded in the memory unit 230, the noise removal system 200 recognizes the activity pattern of the subject and searches the previously generated filter information from the memory unit 230, then removes the noise of the bio signal by using the searched filter information at one time.

The present invention may be embodied on computer-readable storage media encoded with processing instructions for causing a processor to execute methods according to various embodiments of the present invention. The media may also include, alone or in combination with the program instructions, data files, data structures, and the like. Examples of computer-readable media include magnetic media such as hard disks, floppy disks, and magnetic tape; optical media such as CD ROM disks and DVD; magneto-optical media such as optical disks; and hardware devices that are specially configured to store and perform program instructions, such as read-only memory (ROM), random access memory (RAM), flash memory, and the like. The media may also be a transmission medium such as optical or metallic lines, wave guides, etc. including a carrier wave transmitting signals specifying the program instructions, data structures, etc. Examples of processing instructions include both machine code, such as produced by a compiler, and files containing higher level code that may be executed by the computer using an interpreter. The described hardware devices may be configured to act as one or more software modules in order to perform the operations of the present invention.

Accordingly, according to the noise removal method of the present embodiment, an applied filter for each section of a bio signal is determined according to the activity pattern of the subject, thereby maximizing efficiency of the removal of noise. In addition, a problem of removing only noise within certain limits may be solved and an effect of removing an electromyogram signal, which functions as a noise component, measured together with an electrocardiogram signal may be acquired.

According to the above-described embodiments of the above-described embodiments of the present invention, a noise removal method and system using a change in activity pattern may be provided, in which a filter for removing noise components included in a bio signal is selected according to the activity pattern of the subject, thereby removing baseline drift and an electromyogram signal, which functions as a noise component, in sensing an electrocardiogram signal.

Also, according to the above-described embodiments of the present invention, a noise removal method and system using a change in activity pattern may be provided, in which a filter required in removing noise is determined by analyzing a part of the bio signals sensed from the subject and the determined filter is applied to a sensed bio signal, thereby quickly removing the noise.

Also, according to the above-described embodiments of the present invention, a noise removal method and system using a change in activity pattern may be provided, in which a bio signal is converted from the time domain into the frequency domain to identify a frequency band including a noise component and easily designate a filter filtering a noise component in the frequency band.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A method of removing noise by using a change in an activity pattern, comprising:

recognizing an activity pattern of the subject using an activity sensor;

sensing a first bio signal corresponding to the activity pattern from the subject using an electric potential sensor;

recognizing a noise generation pattern according to the activity pattern by analyzing a noise component for each section of the first bio signal;

selecting filter information for each section according to the noise generation pattern;

storing the filter information selected for each section in association with the activity pattern to a memory unit; and removing noise from a second bio signal sensed from the subject by applying the stored filter information, wherein the removing the noise of the second bio signal comprises:

recognizing an activity pattern of the subject corresponding to the second bio signal;

searching the memory unit for filter information corresponding to the recognized activity pattern for the second bio signal; and removing noise from the second bio signal by applying a filter designated by a result of the searching of the memory for the filter information with respect to a certain section of the second bio signal, of plural sections of the second bio signal.

2. The method of claim 1, wherein activity patterns of the subject are recognized from acceleration movement detections of the subject.

3. The method of claim 1, wherein the recognizing the noise generation pattern comprises:

transforming the first bio signal from a time domain to a frequency domain; and identifying a noise component from the transformed first bio signal and checking a frequency band of the identified noise component.

4. The method of claim 3, wherein, in the transforming the first bio signal from the time domain to the frequency domain, the first bio signal is transformed into the frequency domain by one of short time Fourier transform and wavelet transform.

5. The method of claim 3, wherein, in the selecting filter information, a filter eliminating a signal with respect to the frequency band of the identified noise component is determined.

6. The method of claim 1, wherein one of the first and second bio signals is sensed by a sensing unit removably contacting a part of the subject.

7. The method of claim 1, wherein the first bio signal is the same as the second bio signal.

8. A method of removing noise by using a change in an activity pattern, comprising:

recognizing an activity pattern of the subject using an activity sensor;

sensing a first bio signal corresponding to the activity pattern from the subject using an electric potential sensor;

recognizing a noise generation pattern according to the activity pattern by analyzing a noise component for each section of the first bio signal;

selecting filter information for each section according to the noise generation pattern;

storing the filter information selected for each section in association with the activity pattern; and removing noise from a second bio signal sensed from the subject by applying the stored filter information, wherein the identified noise component includes one of baseline drift and an electromyogram signal, and the selecting filter information comprises:

determining a high pass filter as a filter eliminating a baseline drift; and determining a low pass filter as a filter eliminating an electromyogram signal.

9. A system for removing noise by using a change in an activity pattern, comprising:

a motion sensing unit recognizing an activity pattern of the subject using an activity sensor;

a bio sensing unit sensing a first bio signal corresponding to the activity pattern from the subject using an electric potential sensor;

a filter information generation unit recognizing a noise generation pattern according to the activity pattern by analyzing a noise component for each section of the first bio signal and selecting filter information for each section according to the noise generation pattern; and a memory unit storing the filter information selected for each section in association with the activity pattern; and a filtering unit removing noise from a second bio signal sensed from the subject by applying the stored filter information, wherein the filtering unit recognizes an activity pattern of the subject corresponding to the second bio signal, searches the memory unit for filter information corresponding to the recognized activity pattern for the second bio signal, and removes noise from the second bio signal by applying a filter designated by a result of the searching of the memory unit for the filter information, with respect to a certain section of the second bio signal, of plural sections of the second bio signal.

10. A system for removing noise by using a change in an activity pattern, comprising:

a motion sensing unit recognizing an activity pattern of the subject using an activity sensor;

a bio sensing unit sensing a first bio signal corresponding to the activity pattern from the subject using an electric potential sensor;

a filter information generation unit recognizing a noise generation pattern according to the activity pattern by analyzing a noise component for each section of the first bio signal and selecting filter information for each section according to the noise generation pattern; and a filtering unit storing the filter information selected for each section in association with the activity pattern and removing noise from a second bio signal sensed from the subject by applying the stored filter information, wherein the filtering unit comprises:

a high pass filter eliminating baseline drift as the noise component; and a low pass filter eliminating an electromyogram signal as the noise component.

11. A computer-readable storage medium encoded with processing instructions for causing a processor to execute a method of removing noise by using a change in an activity pattern, the method comprising:

recognizing an activity pattern of the subject using an activity sensor;

sensing a first bio signal corresponding to the activity pattern from the subject using an electric potential sensor;

recognizing a noise generation pattern according to the activity pattern by analyzing a noise component for each section of the first bio signal;

selecting filter information for each section according to the noise generation pattern;

storing the filter information selected for each section in association with the activity pattern to a memory unit; and removing noise from a second bio signal sensed from the subject by applying the stored filter information, wherein the removing of the noise of the second bio signal comprises:

recognizing an activity pattern of the subject corresponding to the second bio signal;

searching the memory unit for filter information corresponding to the recognized activity pattern for the second bio signal; and removing noise from the second biosignal by applying a filter designated by a result of the searching of the memory unit for the filter information, with respect to a certain section of the second bio signal, of plural sections of the second bio signal.

* * * * *